US010052474B2

(12) United States Patent
Keyser et al.

(10) Patent No.: US 10,052,474 B2
(45) Date of Patent: Aug. 21, 2018

(54) INTRAVENOUS CATHETER WITH PRESSURE ACTIVATED VALVE

(71) Applicant: I-V Access Technology Inc., Fresno, CA (US)

(72) Inventors: Stephen Richard Keyser, Fresno, CA (US); Jessie Delgado, Durham, NC (US); Theodore J. Mosler, Raleigh, NC (US)

(73) Assignee: I-V Access Technoiogy, Inc., Los Osos, CA (US)

( * ) Notice: Subject to any disclaimer, the term of this patent is extended or adjusted under 35 U.S.C. 154(b) by 244 days.

(21) Appl. No.: 14/660,151

(22) Filed: Mar. 17, 2015

(65) Prior Publication Data

US 2015/0265827 A1 Sep. 24, 2015

Related U.S. Application Data

(60) Provisional application No. 61/954,967, filed on Mar. 18, 2014, provisional application No. 62/111,465, filed on Feb. 3, 2015.

(51) Int. Cl.
| | |
|---|---|
| *A61M 39/26* | (2006.01) |
| *A61M 39/10* | (2006.01) |
| *A61M 39/24* | (2006.01) |
| *A61M 5/32* | (2006.01) |

(52) U.S. Cl.
CPC ......... *A61M 39/26* (2013.01); *A61M 5/3273* (2013.01); *A61M 39/1011* (2013.01); *A61M 39/24* (2013.01); *A61M 2039/1077* (2013.01); *A61M 2039/242* (2013.01); *A61M 2039/246* (2013.01); *A61M 2039/2426* (2013.01); *A61M 2039/2433* (2013.01); *Y10T 29/49826* (2015.01)

(58) Field of Classification Search
CPC ...... A61M 39/10; A61M 39/24; A61M 39/02; A61M 2039/2406; A61M 2039/2426; A61M 2039/2433; A61M 2039/244; A61M 2039/246; A61M 2039/247; A61M 2039/261; A61M 2039/263; A61M 2039/2473

See application file for complete search history.

(56) References Cited

U.S. PATENT DOCUMENTS

| | | | |
|---|---|---|---|
| 4,387,879 A | 6/1983 | Tauschinski | |
| 5,843,046 A * | 12/1998 | Motisi | A61M 39/0606 604/247 |
| 5,957,898 A * | 9/1999 | Jepson | A61M 39/045 128/912 |
| 5,967,490 A | 10/1999 | Pike | |
| 8,105,288 B2 | 1/2012 | Keyser et al. | |

(Continued)

OTHER PUBLICATIONS

International Search Report for related international application No. PCT/US2015/020968.

*Primary Examiner* — Andrew Gilbert
(74) *Attorney, Agent, or Firm* — Levine Bagade Han LLP

(57) ABSTRACT

The anti-back-flow devices and methods prevent fluid from leaking proximally from a catheter, but allow ready access to the catheter using any male luer device. The devices include proximal surfaces that urge open a valve in response to force from a male luer tip. The valves are associated a female luer hub and adapted to function with standard and typical non-standard male luer fittings.

8 Claims, 11 Drawing Sheets

(56) References Cited

U.S. PATENT DOCUMENTS

| | | | |
|---|---|---|---|
| 8,579,870 B2 * | 11/2013 | Willis | A61F 5/445 604/167.04 |
| 8,591,469 B2 * | 11/2013 | Keyser | A61M 25/0606 604/164.1 |
| 2004/0193118 A1 | 9/2004 | Bergeron | |
| 2005/0256460 A1 | 11/2005 | Rome et al. | |
| 2008/0027389 A1 | 1/2008 | Hiejima | |
| 2008/0172003 A1 * | 7/2008 | Plishka | A61M 39/045 604/249 |
| 2009/0287154 A1 | 11/2009 | Harding et al. | |
| 2013/0204226 A1 * | 8/2013 | Keyser | A61M 39/26 604/506 |
| 2014/0058357 A1 | 2/2014 | Keyser et al. | |
| 2015/0038910 A1 | 2/2015 | Harding et al. | |

* cited by examiner

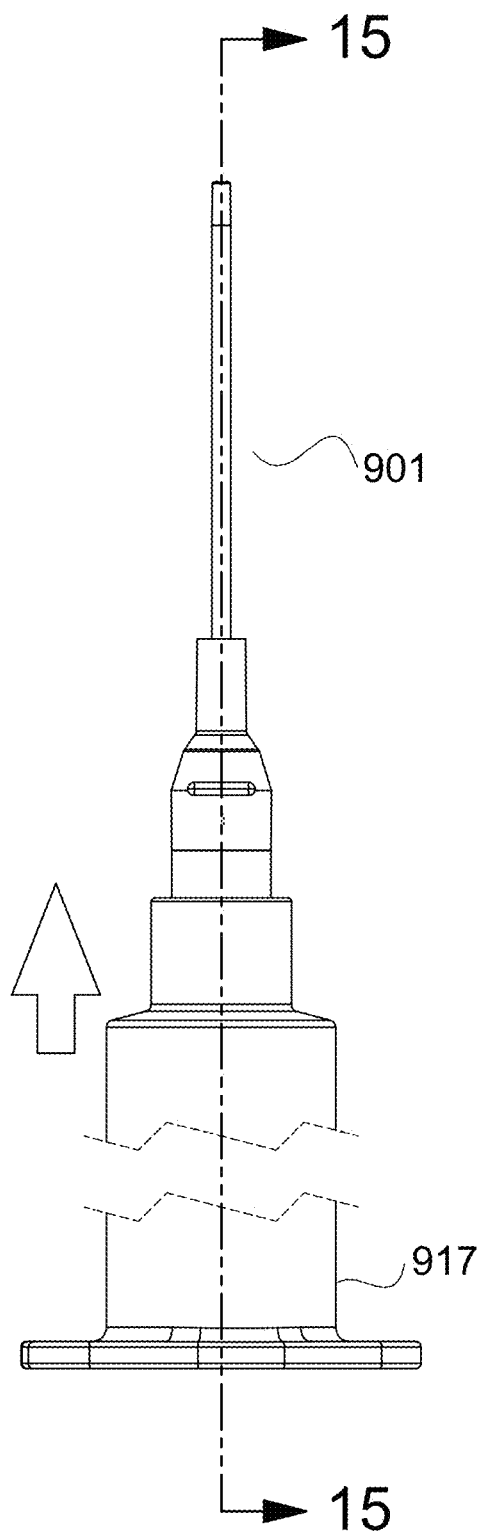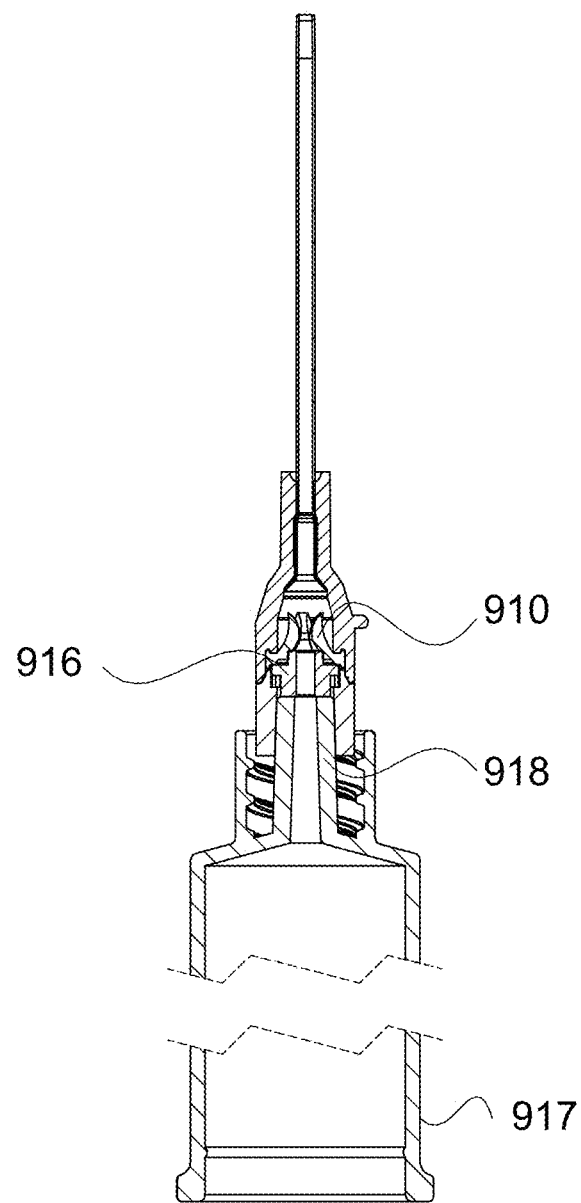
Fig. 14                    Fig. 15

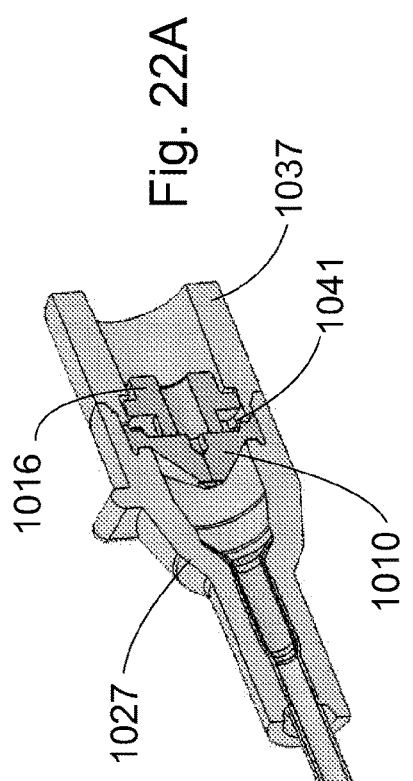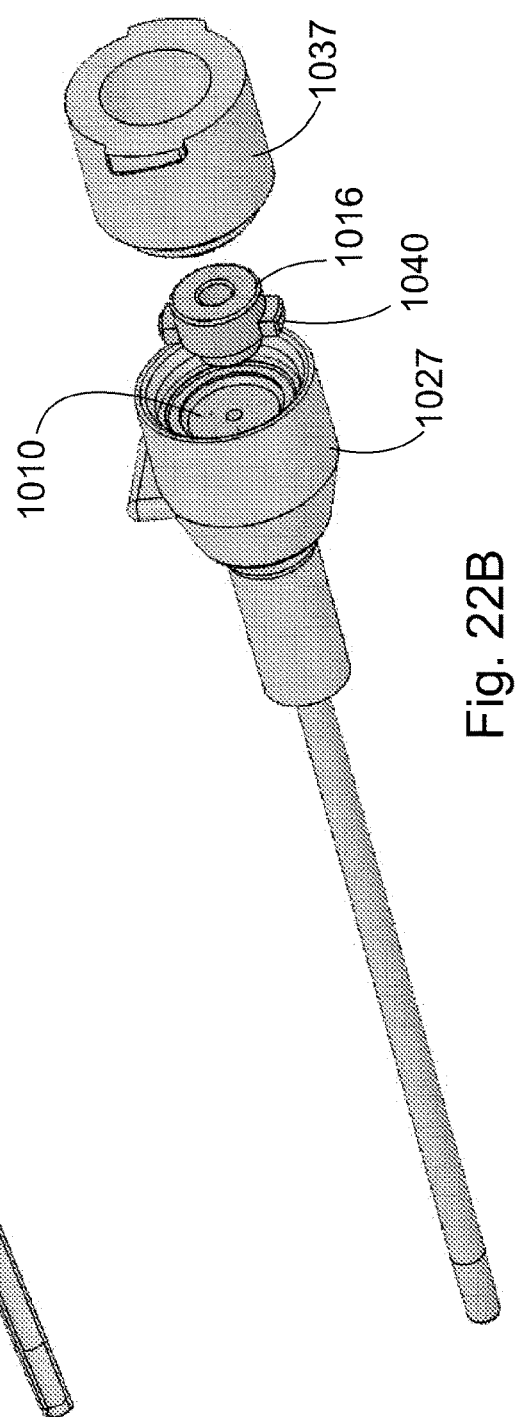

INTRAVENOUS CATHETER WITH PRESSURE ACTIVATED VALVE

CROSS-REFERENCE TO RELATED APPLICATIONS

This application claims priority to and benefit of a prior U.S. Provisional Application No. 61/954,967, Intravenous Catheter with Pressure Activated Valve, by Stephen Keyser and Theodore J. Mosler, filed Mar. 18, 2014 and of U.S. Provisional Application No. 62/111,465, Intravenous Catheter with Pressure Activated Valve, by Stephen Keyser and Theodore J. Mosler, filed Feb. 3, 2015. The full disclosure of the prior applications is incorporated herein by reference.

FIELD OF THE INVENTION

The invention is directed to, e.g., devices and methods for preventing back flow from a catheter. The devices include valve mechanisms and adaptors providing opening of a catheter valve on insertion of a male luer fitting. Methods include provision of the catheter devices, inserting a male luer into the device wherein the luer presses a proximal valve surface or adaptor with the force transmitted to urge opening of a resilient valve.

BACKGROUND OF THE INVENTION

Early technology for vascular access required surgical opening of the skin, viewing of the vessel to be catheterized, and placement, under sterile procedure of a stainless steel needle. After the insertion process, the skin was approximated and the access site covered to prevent infection. The process required a competent physician, and was indicated only in rare instances when the patient required intravascular sustenance or required replacement fluids in association with major surgery.

With many of the described catheterization technologies, blood contamination was a risk when the intra-vascular catheter was inserted. Blood flashback often escaped the catheter hub when the guide needle was removed and before the intra-vascular solution tubing could be connected, thus exposing the caregiver and patient to blood leakage. Several notable valve designs have been patented to reduce this blood leakage. For example, in U.S. Pat. No. 4,387,879, Tauschinski describes a self-sealing elastomeric disc that can be incorporated into a connector body to interface with a parenteral supply solution and an intra-vascular catheter. Similarly, Motisi et al, describe a one way valve in the body of a catheter apparatus in U.S. Pat. No. 5,843,046. However, the necessity of a plunger and introduction of needle or tubing through the plunger decreases the inside diameter of the catheter and reduces the fluid flow rates for this design. An "O" ring in the valve can prevent leakage from around the plunger, but this decreases the inside diameter of the large bore catheter. The valve is held in place by a "cap" which puts its placement deeper into the throughbore, out of reach of conventional intra-vascular tubing or conventional syringes. The "cap" also prevents connection to conventional tubing or conventional syringes. This valve is bulky and decreases the size of the intra-vascular catheter. It also cannot be opened by insertion of conventional devices used by those skilled in the art.

I-V Access Technology, Inc. (IVAT) has intellectual property for a peripheral IV catheter that incorporates an automatic needle retraction mechanism (U.S. Pat. Nos. 8,105,288 and 8,591,469) to retract or withdraw the guide needle when the vein is accessed, a dilator to expand the lumen created by the guide needle (also in US patent divisional application Quine docket 138-000112US), and a pressure activated fluid flow control valve (US patent application US-2013-0204226-A1) to prevent blood leakage when the needle or needle/dilator assembly is fully withdrawn from the catheter assembly. The valve is opened and IV therapy administered through the catheter and into the vasculature when a male luer fitting is inserted into the proximal opening of the catheter hub and contacts the proximal side of the valve.

Although the specific design of the male luer fitting is standardized by ISO, in practice the manufacturers of IV fittings, luer connectors, and syringes produce their products with the male luer geometry sometimes deviating significantly from the ISO standard. As a result, the degree to which the male luer fitting contacts the proximal side of IVAT's valve can vary functionally from an inability to open the valve (no contact at all) to damaging the valve from a shearing of the valve against the catheter hub distal to the valve.

Other manufacturers who produce IV catheters with integrated valves have incorporated a separate slidable adapter piece within the catheter hub that, as the male luer is inserted, it contacts the adapter piece which is axially displaced and penetrates the slits in the valve, thereby opening the fluid flow pathway. The adapter piece that penetrates the slits is generally conical in shape, which allows the adapter to readily open the valve without excessive force, and, when the male luer is removed (e.g. when medication injection through a syringe is completed) the valve exerts an elastic force on the adapter to axially displace the adapter and close the valve to fluid flow. The adapter piece, while considered a necessity to accommodate various male luer geometries and dimensional variations, adds cost and complexity to the manufacturing of the IV catheter. The extra component requires extra material, tooling, and labor costs to produce and potentially additional costs for assembly.

In light of the problems remaining in the art, it would be beneficial to have catheter devices well adapted to receive both standard and non-standard male luer fittings. It would be desirable to have sanitary catheter fittings that seal with non-standard male luers while allowing automatic opening of valves facilitating withdrawal or injection of fluids. Simplified methods and component configurations are needed to allow ready assembly of catheter devices containing a variety of elements finely crafted from a variety of materials. The present invention provides these and other features that will be apparent upon review of the following.

SUMMARY OF THE INVENTION

The present invention relates generally, e.g., to the field of peripheral vascular access and more specifically to devices by which sanitary access can be provided to, e.g., intra-vascular catheters. The inventions include methods and devices that allow, e.g., a flow path to be created on insertion of a male luer into a female luer fitting associated with a catheter.

Generally, the devices include normally closed resilient valves that can be urged open by the insertion force of a male luer fitting. The pressure-actuated catheter assemblies can include a device for adapting a male luer fitting to a catheter so that the presence of the luer automatically opens the anti-back-flow valve of the catheter.

In one embodiment, an annular body on the proximal side of the valve interacts with the male luer to force open the normally closed valve. For example, the self-closing valve can include a proximal annular body defining a proximal tapered recess, distal convex surface, and one or more slits in the distal surface running to the proximal tapered recess and defining two or more cusps. Optionally, the valve can include a radial mounting flange. In many embodiments, the valve is a unitary structure made of a resilient material. The annular body can have a proximal contact surface comprising an outer diameter and an inner diameter, wherein the inner diameter is less than an outer diameter of a standard male luer fitting distal surface, e.g., so that the contact surface matches up to receive forces from the luer fitting. The valve can be adapted so that when the proximal contact surface is forced distally the resilient material of the valve distorts to separate the two or more cusps, creating a path of fluid flow between the proximal recess and the distal surface. The valve is typically mounted between a female luer hub and the catheter section. The valve is usually a resilient normally closed cusp valve.

In optional features, the valve can include a rigid flange embedded at the proximal contact surface of the annular body, to more distinctly contact the luer tip. The valve distal convex surface can be a conical surface. The valve can be adapted so that when the proximal contact surface is forced distally the resilient material of the valve distorts to separate the two or more cusps while creating a path of fluid flow between the proximal recess and the distal surface. The device can further include a catheter section positioned distal from the valve and comprising a catheter hub and catheter.

In many devices, an adaptor (valve actuator) can be provided to interact optimally with the valve at the distal end, but functionally receive diverse male luers at the other end. For example, the device can include a female luer hub having an inner central channel comprising a proximal tapered receiver (e.g., female luer fitting) for a male luer connector; an adaptor located in the central channel and comprising a proximal contact surface, adaptor body, and a distal contact surface; and, two or more struts each extending between the hub and the adaptor body. The struts allow the adaptor to move axially various distances, e.g., depending on the length of the male luer fitting. The adaptor and valve are usually grouped in an assembly with a catheter section (catheter hub and catheter). The valve is commonly mounted between the hub and catheter section. Optionally, the actuator can be mounted in the catheter hub or in a separate actuator hub proximal from the catheter hub. Optionally, the actuator (adaptor) can be integral (formed unitary) to a hub or mounted into a hub after separate fabrication of the actuator and hub. In some embodiments, the proximal contact surface of the valve is an annular body, e.g., in contact with the distal end of the adaptor.

In a preferred embodiment, the female luer hub, struts, and adaptor comprise a unitary structure. Typically, the unitary structure is fabricated from other than a resilient material, rubber, or silicone, e.g., with the unitary structure fabricated as a single piece of a firm thermoplastic. Preferably, there are two or more struts that do not run directly radially between the adaptor and hub. Alternately, the adaptor is a separate element of the device, e.g., with "legs" adapted to slide in hub grooves in its axial movements.

The adaptor functions to adapt between the end of the male luer and the proximal contact surface of the valve. Typically, the outer diameter of the adaptor proximal contact surface is equal or less than an outer diameter of a male luer distal tip, and the outer diameter of the adaptor distal contact surface is equal or less than outer diameter of the adaptor proximal contact surface. Usually, the valve is biased against fluid flow proximally, and the valve has a proximal contact surface positioned distal from the adaptor.

The devices can be used in methods of injecting or withdrawing fluids with a male luer device. A method of providing fluid contact between a male luer fitting and a catheter can include, e.g., providing a luer connector, a valve, and a catheter section and using it to exchange fluids safely with a male luer device. For example, the luer connector can include a female hub having an inner central channel comprising a proximal tapered receiver for a male luer connector; an adaptor located in the central channel and having a proximal contact surface, adaptor body, and a distal contact surface; and, two or more struts each extending between the hub and the adaptor body. Alternately, the adaptor can have two or more radially extending legs configured to slide axially in complimentary hub grooves. The valve is normally closed and biased against proximal flow. The valve comprises a proximal contact surface and is positioned distal from the adaptor distal contact surface. A catheter section is positioned distal from the hub and comprises a catheter hub and catheter. A male luer fitting is inserted into the tapered receiver until the distal end of the male luer contacts the adaptor proximal contact surface. When the male luer fitting is further inserted, the adaptor is forced distally against torsional resistance of the struts. The adaptor in turn contacts the proximal surface of the valve forcing open the valve and creating a path of fluid contact between the male luer and the catheter.

In the methods, the valve can have an annular body interacting with the luer contact force to open the valve. For example, the method can include providing fluid contact between a male luer fitting and a catheter by providing a luer connector, a valve, and a catheter section; wherein the luer connector comprises a female hub having an inner central channel comprising a proximal tapered receiver adapted to receive a male luer connector; providing a normally closed valve biased against proximal flow, the valve comprising: a proximal annular body defining a proximal tapered recess, a radial mounting flange, a distal convex surface, and one or more slits in the distal surface running to the proximal tapered recess and defining two or more cusps; providing a catheter section positioned distal from the hub and comprising a catheter hub and catheter; inserting the male luer fitting into the tapered receiver until a distal end of the male luer contacts a proximal contact surface of the proximal annular body; and further inserting the male luer fitting, distorting the proximal annular body, which in turn transmits force distally radially displacing the two or more cusps thereby opening the valve and creating a path of fluid contact between the male luer and the catheter. The method can further include removing the male luer from the tapered receiver, wherein pressure from the annular body is released in the resilient valve allowing the valve back to the normally closed position.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a component" can include a combination of two or more components; reference to "fluids" can include mixtures of fluids, and the like.

Although many methods and materials similar, modified, or equivalent to those described herein can be used in the practice of the present invention without undue experimentation based on the present specification, the preferred materials and methods are described herein. In describing and claiming the present invention, the following terminology will be used in accordance with the definitions set out below.

The term "vessel", as used herein, refers to a conduit through which a fluid travels. For example, a typical vessel can be a blood vein, artery, or lymph vessel. In some aspects of the invention, a vessel can be a segment of the digestive tract, a gland duct, or a cerebral-spinal fluid chamber. In a more generic context, a vessel can be a chamber or conduit containing a fluid.

The "distal" end of a device component is the end closest to the vessel or patient, in use, e.g., the end of the component intended to enter a vessel first. For example, the distal end of a needle is the piercing end. The distal end of a catheter is the end first intended to be inserted into a patient's skin or vessel.

The "proximal" end is the end of the device component oriented opposite the distal end. For example, the proximal end of an adaptor is the end intended to first contact the male luer fitting.

A "resilient" material tends to return to its original position when a deforming force is removed. Typical resilient materials include elastic materials, rubber, silicone rubber, and/or the like.

An "axis", as typically used herein, is an imaginary line parallel to and in the center of a tubular device. The term axial thus refers to the direction that runs parallel to the axis, e.g., of a tubular device. Two components are concentric when their major axes are coincident. Axial movement is a movement along direction aligned (parallel) with the axis. The axis of a flexible tube can be considered to be a line running down the center of the tube at any particular cross section, e.g., following the course of the flexible tube.

A hub is a part of a device, such as a catheter, at the proximal end, which typically flares out to a larger external diameter, e.g., to aid in technician handling. The hub can provide a base for mounting or employing features, such as detents or needle retractor devices, catches, valves, grips, etc. The hubs can provide functional interaction of the catheter or catheterization device with external devices, such as, e.g., male luer fittings, trocars, syringes, fluid administration lines, optic fibers, vacutubes, etc.

An intra-vascular (IV) catheter is typically as is understood in the art. The IV catheter can include a long, slender, tubular body, usually made of a flexible plastic and intended for insertion into a patient's body. The tubular body has a hub at the proximal end for connection and interaction with other elements of the overall catheter assembly.

A tapered topography is as known in the art. For example, a tapered channel has a gradual diminution of interior diameter along the axis.

A thermoplastic, or thermosoftening plastic, is a polymer that becomes pliable or moldable above a specific temperature, and returns to a solid state upon cooling.

The term "luer" fitting is as known in the art. There are ISO standard fittings, and luers that diverge somewhat from the standard. The luer taper is a standardized system of small-scale fluid fittings used for making leak-free connections between a male-taper fitting and its mating female part on medical and laboratory instruments, including hypodermic syringe tips and needles, or stopcocks and needles. There are two varieties of luer taper connections: luer-lock and luer-slip. Luer-lock fittings are securely joined by means of an external tabbed hub on the female fitting which screws into threads in a sleeve on the male fitting. Luer-slip fittings simply conform to luer taper dimensions and are pressed together and held by friction (they have no threads).

The term "unitary" as used herein, refers to an object consisting of a single piece. For example, an object formed from a single injection molding, e.g., without assembly or addition of further parts has a unitary structure. Molded or billet structures are typically unitary.

The terms "adaptor" and "valve actuator" are used interchangeably herein. The Actuators configured for positioning between a resilient valve and, e.g., external device, such as a syringe male luer, to transmit forces between the two, as described herein.

A valve is a device that controls the flow of fluid through the apparatus.

BRIEF DESCRIPTION OF THE DRAWINGS

The drawings here shown include exemplary embodiments of the invention. It is to be understood, however, that the present invention may be embodied in various forms. Some aspects of the invention may be shown exaggerated or enlarged in the drawings to facilitate an understanding of the invention.

FIG. 14 shows the first end 901 engaged with an ISO 594 compatible luer equipped syringe 917 that has advanced axially into the catheter/actuator hub.

FIG. 15 provides a cross-section view of the FIG. 14 elements. In this position, the luer 918 of the ISO 594 compatible luer equipped syringe 917 has come in contact with the valve actuator 916 which has been advanced forward axially causing the actuation (opening) of the valve 910.

FIGS. 22A and 22B are schematic diagrams showing a distal end catheter assembly with the resilient valve received in the catheter hub and the actuator in a slide fit interaction with an actuator hub comprising a female luer fitting.

DETAILED DESCRIPTION

Figure 1:
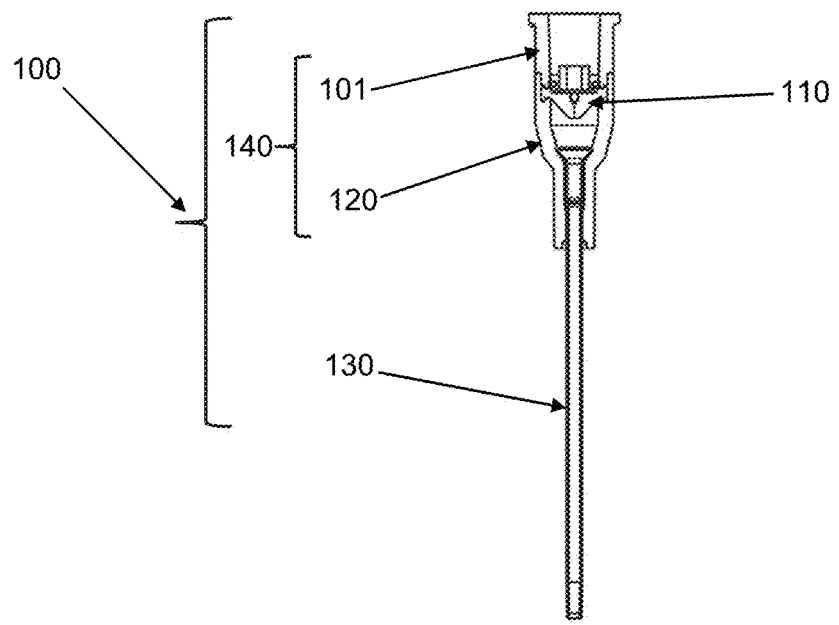
FIG. 1 is an axial cross-sectional diagram of an exemplary catheter assembly including a resilient normally closed valve and adaptor to functionally receive standard and non-standard male luer fittings.

The present inventions are directed to devices and methods to reduce contamination of catheters, and to enhance safety and convenience for catheter technicians. The devices adapt to receive male luer devices of standard dimensions and also typical variants on the market. The methods include provision of the present devices and inserting therein a distal male luer tip to contact a proximal valve surface. The valve surface can be compliant and movable in a range of axial distances to conform to male luers of various dimensions. The male luer can be further advanced to force open a cusp valve allowing fluids to be retrieved or injected through the valve in fluid contact with the lumen of the catheter. Valve actuators can be provided to aid in efficient operation of the valve and enhance the range of external devices compatible with the catheter function.

Device for Adapting Various Male Luers to a Catheter

The devices presented herein are adapted, e.g., to receive a variety of male luer connectors providing sealed connections to catheter devices. The devices accommodate male luer ends of various lengths, tapers and widths within ranges around the ISO standard. The devices not only provide adequate seal, but allow the various different male luer fittings to actuate a catheter sealing valve to establish a fluid connection between the catheter and the male luer device.

Adaptor Structures.

In one aspect, a device to receive male luer fittings has a unitary self-retracting adaptor configured for access by male luers having shorter and narrower dimensions, while also accommodating luer fittings with longer or wider dimensions. The adaptor is suspended on torsion bars in the hub of a female luer fitting. The adaptor (valve actuator) can have a proximal surface sized to functionally contact a variety of male luer tip internal diameters (ID) and outer diameters (OD). The adaptor, e.g., suspended on torsion bars for axial movement is adapted to adjust axial position depending on the position of the male luer when properly fitted into the female luer. The distal end of the adaptor is configured to effectively press a proximal surface of a resilient valve, opening to provide flow in either direction between the male luer and a distal catheter.

In another aspect, the actuator can have two or more radial tabs configured to slide in slots inside a catheter hub, or in a separate actuator hub. An actuator hub can be located proximal to the catheter hub. For convenience of manufacture, the catheter hub and actuator hub can capture the valve and actuator in between when the distal actuator hub is mounted onto the proximal catheter hub.

The female proximal end of the adapting device can include a female luer hub element, a movable adaptor, and two or more torsion bar struts (or actuator tabs) to movably suspend the adaptor within the center axis of the hub. Alternately the adaptor can be mounted with tabs (legs) in slots of grooves of the hub. In preferred embodiments, the three elements of the device for adapting a male luer fitting to a catheter are a unitary structure, e.g., with the female luer, adaptor, and struts formed from a single piece of thermoplastic. Alternately, the female luer hub and adaptor are separate components, e.g., of an actuator hub or catheter hub.

The female luer can have ISO standard dimensions, e.g., of length, width and taper. However, to be more accommodating to the variety of non-standard male luers, the internal dimensions of the female luer can be non-standard. For example, to receive a shorter than standard length (7.5 mm) male luer the internal axial dimension (length) of the female luer can be shorter, e.g., on the proximal and/or distal end, as compared to standard female luer fittings. To receive wider male luers, the female luer ID can be wider. Although the standard 6% conical taper is preferred, the taper can be adjusted, e.g., to allow receipt of male luers with greater or lesser tapers. The above-described modifications can allow the variety non-standard luers to be received and seal. Meanwhile, the movable adaptor can allow the device to accept a wide range of luer depth of insertion, male luer width, and/or male luer taper.

The internal space of the female luer fitting can be modified to accommodate a wider range of male luer fittings. For example, the axial taper of the conical internal space can range from less than 4% to more than 10%, from 4.5% to 9%, from 5% to 8%, from 5.5% to 7%, or about 6%. The length of the female luer fitting internal space can be from less than 1 mm to more than 15 mm, from 2 mm to 12 mm, from 4 mm to 10 mm, from 6 mm to 9 mm, or about 8 mm The proximal internal diameter can range from less than about 1.5 mm to more than 6 mm, from 2 mm to 5 mm, from 2.5 mm to 4 mm, or about 3.5 mm The internal diameter at the distal end can range from less than about 1.0 mm to more than 5 mm, from 1.5 mm to 4 mm, from 2 mm to 3 mm, or about 2.5 mm. In some embodiments, the taper is not uniform, e.g., to adjust for different male luer dimensions in a shorter distance.

The female luer fitting can be part of an overall proximal hub of the adapting device. The hub structure can provide the walls of the internal female luer fitting space. The hub can include male or female threads to allow it to functionally interact with complementary threads of a male luer device to be attached to the catheter.

Typically, the hub (defining female luer space) is fabricated as a unitary structure including the adaptor, optionally with struts. Optionally, the one or more of the parts can be fabricated separately and assembled into a functional unit. Although the unitary structure is preferably not significantly resilient (e.g., compressible), it can be somewhat deformable. In preferred embodiments, the unitary structure is not a rubber material, though it could be. In preferred embodiments, the unitary structure is a solid material, e.g., such as a metal, plastic, composite, ceramic, and/or the like. Preferably, the unitary structure is fabricated from a plastic, such as, e.g., a thermoplastic or, e.g., acrylic plastic, nylon, polybenzimidazole, polyethylene, polypropylene, polystyrene, polyvinyl chloride, Teflon, and/or the like.

Adaptors are typically positioned along the central axis of the hub, suspended with struts. The adaptor is a structure functioning to transmit a force through a distance between the distal tip of, e.g., an inserted male luer and the proximal end of a valve (which valve contact surface is configured to open the valve when pressed distally). The adaptors can be any shape appropriate to functionally contact the inserted male luer tip and the proximal valve contact surface. The adaptor and surrounding environment should be configured to allow fluid flow past the adaptor, e.g., a hollow or indented adaptor cross-section and/or hub space around the adaptor. Because many parts in such devices (interacting conduits) are cylindrical, the cross section across the adaptor axis often conforms to this with a round or oval shape, particularly at the contact surfaces. In alternate embodiments, a cross section of an adaptor can be square, star shaped, a cross, etc. as long as the contact surface makes sufficient contact with the male luer or valve and the body of the adaptor is strong enough to transmit adequate forces axially to open the valve. Exemplary adaptors are conical, cylindrical, hour glass, box shaped, egg shaped, or the like. In preferred embodiments, the adaptor body is cylindrical, or slightly tapered down in the distal direction.

The adaptors often also perform a function of a conduit between the male luer and the valve. In this role, the adaptor will have, e.g., a central channel running from the proximal end to the distal end of the adaptor (e.g., with an inlet in the distal contact area and outlet in the proximal contact area). The overall shape and dimensions of the channel can vary as long as it furnishes adequate fluid contact between the distal and proximal ends of the adaptor.

The adaptors can be less than 1 mm in length to more than 20 mm, from 1.5 mm to 10 mm, from 2 mm to 5 mm, or about 3 mm in length. The adaptors are typically about the same OD at the luer contact surface as the tip of a male luer. The adaptor end contact surfaces can range in cross section diameter (or greatest traverse) from 1 mm or less to 5 mm or more, from 1 mm to 4 mm, from 2 mm to 3 mm, or about 2.5 mm Adaptors are mounted within the hub on one or more struts. In order to stably mount the adaptor to avoid twisting motions out of the hub central axis, it is preferred to have at least two struts (e.g., 180° opposed), and most preferred to have at least three struts (e.g., spaced every 120°). The adaptor can be mounted to the hub with 1 to more than 24 struts, from 2 to 12, from 3 to 6 or about 4 struts. Alternately, the adaptors can move axially with two or more radial tabs sliding in hub grooves.

The struts act as torsion bars; when they are bent they tend to spring back with opposing force. Because the unitary structure is typically not very resilient, the struts are typically configured to spring back more like a lever than a rubber band. To accentuate this motion, it is preferred to not align the struts with a radial (perpendicular to the central axis), but to align the struts at an angle from the radial. For example, a strut may originate from an inside wall of a cylindrical hub at an angle away from the radial and terminate in a side wall of the adaptor at an angle not perpendicular to the side wall. The average strut path from the hub to the adaptor can be direct, but preferably at an angle from the axis radial. For example, the strut path can be less than 5° to 90° from the radial, from 10° to 75°, from 25° to 60°, from 30° to 50°, or about 45° from the radial. There is typically space between struts, e.g., to allow passage of fluids and to allow free independent movement of the struts. The strut path can include more than one angle relative to the radial (e.g. a serpentine path) to conform to the shape of the inside wall of the cylindrical hub and the outside wall of the adaptor and to reduce stress concentrations on the struts as the adaptor is axially displaced. A cross section of a strut can be any functional shape, such as round, polygonal, oval, etc. However, it can be preferred to have a larger dimension in the axial direction, e.g., to improve rebound force and allow freer fluid flow. Struts can have a length adequate to traverse between the hub and adaptor. For example the struts can be 0.7 mm or less in length to 15 mm or more in length, from 1 mm to 5 mm, from 2 mm to 4 mm, or about 2.5 mm The adapting device can interact with a distal valve. The valve is often mounted between the adapting device and a catheter. In a preferred embodiment, the valve is a resilient, normally closed cusp valve. The valve has a proximal contact surface to receive opening force from the adaptor, and a distal cusp flap convex surface configured to prevent proximal flow of fluids.

Valves.

Valves are mounted between the adaptor structure and catheter, e.g., to prevent back flow out of the catheter and preventing external contamination inflow to the catheter. The valves may allow fluid flow distally in response to a fluid pressure alone, but typically require pressure from a male luer tip or adaptor to force them open. Being cusp flap valves, the valves typically do not allow significant back flow proximally without first being forced open by a force on a proximal valve surface.

The valve can be mounted, e.g., centered in the flow axis of the device. Depending on configuration, the valve may be mounted in the adaptor hub, in a catheter hub, between the adaptor hub and catheter hub, or in its own hub or mounting bracket. In many embodiments, the valve includes a peripheral flange, e.g., press-fit or glued into a surrounding complementary groove.

Resilient valves of the invention typically include a tapered distal surface with slits running to a proximal valve surface. The proximal surface can include a contact surface to receive the distal end of an adaptor. Pressure from the adaptor can lever or deform the valve to force open the distal surface at the slits (see, e.g., the description of resilient valves in application Ser. No. 13/759,643 (published US 2013-0204226).

The valve can have a distal surface and proximal surface, e.g., with one or more slits running through the valve between the distal and proximal surfaces. The proximal surface can have one or more recesses defining a shoulder that acts as a contact surface for opening forces.

In use, a male luer connector is inserted into the female luer fitting of the hub to a point where the distal face of the male luer contacts the adaptor. On further axial movement the luer and adaptor push the valve proximal contact surface distally causing the cusp flaps to swing outwardly, e.g., at a pivot region in the resilient valve material.

The valves often include a convex, e.g., tapered distal surface. The distal surface is preferably uniformly tapered, and more preferably generally conical, e.g., to provide a complimentary contact and minimum dead volumes between the valve flaps and a catheter hub bore, when the valve is in the opened position. The cross sections (across the axis of fluid flow or the axis of the catheter bore) of the recesses can be any shape, as functionally appropriate.

The valves are typically flap valves (comprising two or more cusps) with a resilient bias to a normally closed position. The valves are "one way" valves in that a fluid pressure from the distal side tends to only close the valve harder. The valves are configured to open and separate the cusps when force is applied from the proximal side. Optionally, the valves are closed by a hydraulic back pressure from the distal side of the valve. The valve flaps are defined by the boundaries of the slits. A pivot region, e.g., at the base of the cusps, between the outer extent of a proximal surface (shoulder) lever action arm and the nearest surface of the valve distal surface, can range in thickness from, e.g., more than 5 cm to less than 0.1 mm, from 1 cm to 0.2 mm, 5 mm to 0.25 mm, 1 mm to 0.3 mm, or preferably about 0.4 mm Optionally, the pivot region can be hinged. The pivot region can become somewhat compressed when the conduit is applying force to a valve proximal surface or shoulder. The pivot region can range in thickness from more than 50% the shoulder lever action arm to less than 1%, from 40% to 10%, from 25% to 15%, or preferably about 20% of the shoulder action arm length.

The valve can include a flange useful in mounting the valve in the device, e.g., between the catheter hub and adapting device. The flange can provide a hermetic seal and maintain the valve in a functional relationship relative to the other assembly components, and relative to an external conduit requiring access to the catheter bore.

In many embodiments, the valve can range in width, across the proximal surface, from more than 20 cm to less than 0.5 mm, from 10 cm to 1 mm, from 1 cm to 1.5 mm, from 7 mm to 2 mm, or about 5.5 mm The valve can have a first most distal recess, e.g., in the center of the proximal surface with an ID ranging, e.g., from more than 2 cm to less than 0.25 mm, from 1 cm to 0.5 mm, from 5 mm to 0.7 mm, from 2 mm to 0.9 mm, or preferably about 1 mm.

The valves can be made from any appropriate material. Typically, the valves are made from a resilient material, such as, e.g., a rubber, silicone rubber, a flexible plastic, or other resilient polymer. It is envisioned that valves with the above functions can be made from, e.g., spring loaded mechanically hinged solid materials, but this is typically less preferred for reasons of manufacturing simplicity, reliability and sanitation.

Slits in the valves typically number from one to ten or more. To provide better separation of flaps in the open condition, it is preferred to have at least three slits running through the valve between the distal and proximal surfaces of the valve. Slits are typically two-dimensional or sheet-like cuts through the valve material, e.g., as is commonly understood. Slits can be planar boundaries between valve flaps. Slits can be three dimensional, e.g., described by curving surfaces. A single one-dimensional hole or path is not a slit.

In many embodiments, the valve slits on the distal surface run from the most distal aspect of the distal surface to a point on the distal surface adjacent to the pivot region. On the proximal side of the valve slits typically run from the center (typically most distal) surface of the recess to the pivot region at the outer extent of the shoulder in the first recess. Of course, the slits include sheet-like cuts through the valve between the described surface features. Such complete slits can define functional flaps in the valve. Slits can run, e.g., from 1) a line defined by the most distal point of the distal surface and the most distal point of the proximal recess, to 2) a line defined by a point where the distal surface contacts the catheter bore wall with the valve in the closed position, and a point on the proximal surface that leaves sufficient material to provide an adequate flap mount and pivot, e.g., within 0.1 and 2 mm from the inner hub wall. The slit between these two lines can be any functional shape. However, it is preferred the slit have planar or a curved surfaces.

In some embodiments, it is preferred the slit run laterally on the proximal surface to at least the intersection of the recess and the proximal contact surface, e.g., to provide a tight hermetic seal around an adaptor or luer tip inserted through the second recess. Alternately, the slits can run to a point between the intersection of the recess, e.g., to a point on the proximal contact surface. This can allow freer movement of the flap bases as the valve is forced open. Optionally, the slits can terminate in the recess without reaching the shoulder between the recess and proximal surface. In some embodiments, the slits run to at least the outer edge of the proximal contact surface.

Flaps defined by the slits are typically directed toward the distal end of the catheter. The outer surface of the flaps typically comprise valve distal surfaces. The inner surface of the flaps typically include surfaces defined by the slits, any recess, and/or the proximal contact surface. Because the slits, recess, and proximal surfaces typically run in different directions, the inner surface of the flaps are typically not simple curved surfaces, and most of the inner flap surface does not typically parallel the immediately adjacent outer flap surface, e.g., as shown in the present figures.

The proximal contact surface typically has a shape complimentary to the end of a conduit (adaptor or luer tip) intended to be received; particularly, complimentary to the conduit end and outer circumference near the conduit end. In many cases, the recess is generally cylindrical in shape. The intersection of the recess proximal end and proximal (e.g., contact) surface typically intersects at approximately a right angle. However, the proximal recess sides may be flared out somewhat (at an angle greater than 90 degrees), e.g., to swage, center, and seal a conduit tip introduced therein. In most embodiments, the primary seal between an introduced conduit and the valve is between the conduit end and the proximal contact surface. Optionally, the side surface of the first recess can be configured to function as seal against the outer surface of the conduit, e.g., back from the conduit end. In some cases, the system as a whole can be sealed cooperatively or exclusively by swedging the male luer fitting into the female luer fitting.

In another aspect of the invention, the resilient valve comprises an annular body defining a proximal contact surface configured to directly receive opening pressure from the tip of an inserted male luer. The male luer contacts the annular body at a proximal contact surface, and the pressure causes deformation of the annular body toward the axis and distally. The proximal deformation can enhance the sealing of the annular body on the luer tip. The deformation distally transmits opening force urging open the valve cusps.

The annular body can functionally interact with a wide variety of male luer fittings. The valve can be configured to open the cusps over a short throw of luer progress and then resiliently comply with further advance. In this way, male luers longer or shorter than standard luers can open the valve.

Figure 5:
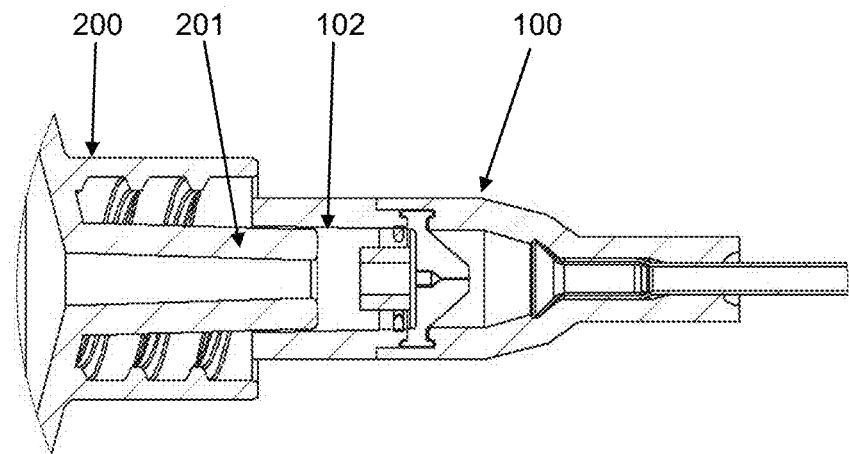
FIG. 5 is a cross sectional diagram of a catheter assembly including an adapting device mounted proximal to a normally closed valve and catheter.
Figure 7:
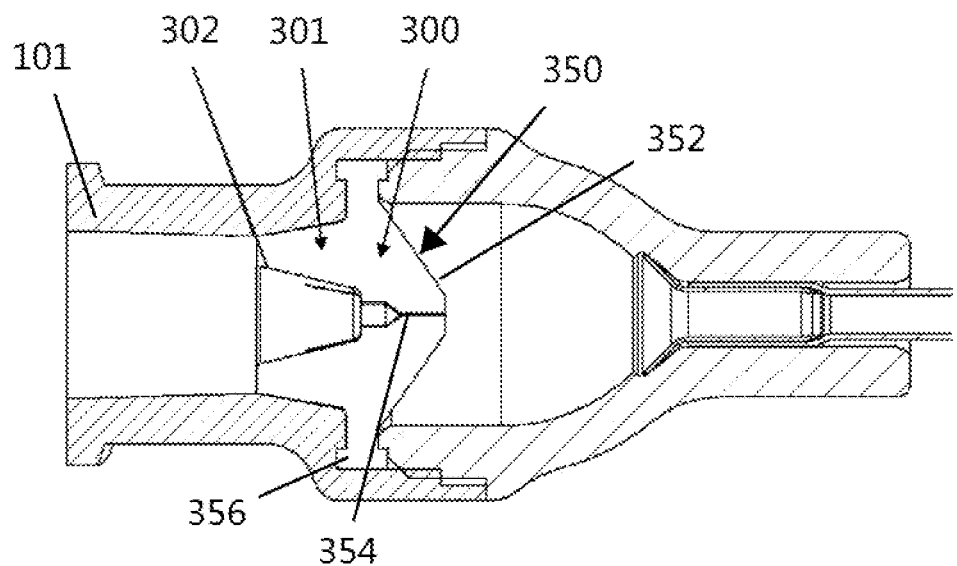
FIG. 7 is a cross sectional diagram of a normally closed valve having an annular body configured to open the valve on pressure from a male luer device.

The valve including the proximal annular body aspect can be essentially as described above in the section on valves (e.g., as shown in FIG. 5), but with the proximal body extending proximally and defining the proximal tapered recess (e.g., as shown in FIG. 7).

The valve can be a unitary resilient valve comprising the annular body, radial mounting flange, convex distal surface, slits between the distal surface and one or more proximal surfaces, and the valve flap cusps defined by the surfaces and slits.

The proximal annular body has a bulk of resilient material that deforms to force open the valve cusps when pressed distally from the proximal contact surface. The inner surface of the annular body typically defines a tapered recess, terminating distally with the proximal surface of the flaps and/or the proximal surface to the first recess. Note, although the annular body defines a "tapered" recess, it is envisioned that the annular body can perform the deformation and opening functions with the inner surface defining other than a tapered space. However, in preferred embodiments, the tapered recess has a wider proximal diameter than the distal end diameter.

The dimensions of the annular body can be any suitable to provide the function of transfer of pressure to open the cusps when pressure is applied to deform the proximal contact surface. The internal tapered recess space described by the annular body is typically tapered. For example, the axial taper of the tapered recess can range from less than 4% to more than 45%, from 6% to 40%, from 12% to 35%, from 20% to 30%, or about 25%. The length of the tapered recess (not counting any optional first proximal recess space) internal space can be from less than 0.5 mm to more than 10 mm, from 1 mm to 6 mm, from 1.5 mm to 5 mm, from 2 mm to 4 mm, or about 3 mm The proximal diameter of the tapered recess can range from less than about 0.5 mm to more than 6 mm, from 1 mm to 5 mm, from 1.5 mm to 3 mm, or about 2 mm The internal diameter at the distal end can range from less than about 0.1 mm to more than 4 mm, from 0.3 mm to 3 mm, from 0.7 mm to 2 mm, or about 1 mm If a first (distal) recess is present, e.g., providing a proximal cusp surface, there can be a shoulder between the first recess and tapered recess, or the tapered recess can transition into the first recess without any angular protrusion at the boundary.

The walls to the annular body can be cylindrical, but typically change as the recess tapers. The thickness of the annular body wall at the proximal contact surface can range from less than 0.5 mm to more than 3 mm, from 0.7 mm to 2 mm or about 1 mm The axial length of the annular body can range from less than 0.7 mm to more than 5 mm, from 1.5 mm to 4 mm or about 3 mm The proximal contact surface of the annular body functions to receive pressure from a male lure tip (or adaptor) and optionally to provide a sealing function. The proximal contact surface typically runs more perpendicular to the axis than parallel. The annular body proximal contact surface is preferably designed to have an outer diameter equal to or greater than the tip of a male luer. The outer diameter of the tapered recess proximal end is typically designed to be equal to or less than the outer diameter of the male luer tip. It is preferred that the outer diameter of the tapered recess proximal end not be much less than the internal diameter of the male luer tip, so as to avoid reducing fluid flows. In some embodiments, the annular body proximal contact surface can be covered with a less resilient material (e.g., such as a thermoplastic or metal flange or washer) for a firm contact less dependent on the shape of various optional male luer tips.

In embodiments employing the annular body in an overall catheter assembly, the resilient valve can be mounted as previously described above. That is, e.g., the valve can be mounted using the mounting flange interacting (e.g., with annular cut outs or grooves) to the female luer hub, adaptor hub, catheter hub, between the female luer hub and catheter hub, or between the adaptor hub and catheter hub.

IV-Catheters.

The present devices are intended to adapt the male luer fittings to catheters. Catheters are typically as are known in the clinical arts, although the present devices are useful in other arts where sealed or sanitary access to a conduit is desired. In many embodiments, the catheter is part of an overall assemble including, e.g., a female luer hub, adaptor device, valve opening to pressure at a proximal surface, and the catheter. In many cases, the catheter has a hub that is attached to (or integral with) a female luer hub, e.g., with the valve in between. Alternately, there can be intermediate features between the catheter hub and proximal female luer.

Catheters of the inventive devices are, e.g., working devices and/or access ports intended for insertion into a vessel. The catheters are typically slidably mounted over the needle or guide dilator of the device and have an outer diameter expanding away (tapering) from the distal catheter tip. That is, in some embodiments the device is designed to accept a guide needle to be inserted therethrough (e.g., past female luer, adaptor, valve and/or catheter) while the catheter is being inserted into a patient. After catheter insertion the needle can be withdrawn, and male luer devices can gain access to the catheter using the pressure actuated valves described herein.

The catheters typically have a constant diameter conduit body proximal to the tapered tip. Such a structure can smoothly and painlessly further enlarge a hole in a vessel wall initially made by the guide needle and optionally expanded by a dilator. In many embodiments, a rigid or flexible catheter can be guided through a vessel wall and/or some distance along the vessel lumen following the path of the guide dilator. Catheters can include a hub configured, e.g., for interaction with other devices of the present catheter assemblies.

Catheter components of the devices are typically flexible or resilient hollow structures with a tapered distal end. In most embodiments of the invention, the catheter is initially slidably mounted over a needle, until at least after the catheter distal tip is situated in a vessel. The catheters can be made from a flexible material, such as, e.g., silicone rubber, polypropylene, rubber, fluorocarbon plastics, and the like. In other embodiments, the catheter can be made from rigid materials, such as stainless steel, a glass, ceramic, rigid plastic, etc. The catheter can be opaque or optionally translucent or transparent, e.g., to allow viewing of blood in the device lumen (e.g., from a needle through-notch, described above). Catheters can range in length, e.g., from about 15 cm to about 0.7 cm, 10 cm to about 1 cm, from about 7 cm to about 2 cm, from about 5 cm to about 3 cm or about 4 cm. The catheters can have an inner diameter ranging, e.g., from about 3 cm to 0.4 mm, from about 2 cm to about 0.5 mm, from about 1 cm to about 0.6 mm, from about 5 mm to about 0.7 mm, from about 2 mm to about 0.8 mm, or about 1 mm Catheter wall thickness is typically configured to suit the intended function of the catheter. The catheter wall typically ranges from about 0.1 mm to about 1 cm, from about 0.5 mm to about 5 mm, from about 0.75 mm to about 2 mm, or about 1 mm.

Catheters of the invention usually have a tapered distal end configured for dilation of structures, such as skin, wall structures, membranes, vessel walls, and the like. In preferred embodiments, the tapered distal catheter tip is relatively thin walled and closely contacts or seals over the outer surface of the guide needle or dilator distally. The wall thickness (and outer catheter diameter) can progressively increase proximally from the tip for some distance. In many embodiments, the catheter outer diameter reaches a desired size (e.g., for performance of the desired catheter function) and continues proximally for some distance with the same outer diameter. The distance from the tapered distal catheter tip to the final maximum distal outer diameter (catheter tapered section) typically ranges from about 30 cm to about 1 mm, from about 20 cm to about 2 mm, from about 10 cm to about 2 mm, from 7 mm to about 3 mm or about 4 mm.

Catheters usually have a hub structure at the proximal end. The hub functions to connect the catheter to other assembly members, such as the female luer hub, adaptor, and/or valve. The interaction with the female luer hub can provide for connection to external devices, such as syringes, IV fluid conduits, surgical devices, electrodes, diagnostic devices, and/or the like.

The catheter hub can optionally provide structures that interact with proximal hubs of the device needle and/or dilator. For example, the catheter hub can include tangs, grooves or cavities that interact with other hub structures to control or limit movement of the needle or dilator.

Providing Fluid Contact Between a Luer and Catheter.

The present methods generally include the steps of inserting a catheter in a vessel, and gaining access with a male luer fitting by pressing the tip of the fitting against the proximal side of a valve that was sealing the catheter. Optionally the male luer presses open the valve through forces transferred by an adaptor between the luer and valve.

A general method of providing fluid contact between an male luer fitting and a catheter can include, e.g., providing an assembly described herein, e.g., comprising a female luer fitting, a pressure actuated valve and catheter; inserting the catheter into a vessel; pushing a male luer device into the female luer fitting and pressing the luer tip against a proximal surface of the valve forcing open the valve flaps; and, injecting or withdrawing a fluid through the valve. The male luer can be removed, allowing the valve to resiliently return to a normally closed sanitary condition.

In one embodiment, variations of male luers from the ISO standard are accommodated by use of an adaptor between the luer and the valve. For example, an adaptor can be movably mounted in the fluid flow axis of the assembly. The distal end of the adaptor can be configured to optimally interact with the valve in the operation of opening and closing. The proximal end of the adaptor can be configured to functionally interact with a wide variety of male luer fittings, e.g., having non-standard variants of length, taper, tip width and wall thickness. The adaptor can be hollow to allow passage of fluids.

In practice, the catheter assembly, including a guide needle, the female luer, adaptor, valve, and catheter are all typically provided and a functional assembly. A technician inserts the distal piercing end of a guide needle through a patient's skin and through the wall of a blood vessel. The device can be urged distally by the technician so that the distal tapered end of the catheter wedges into the vessel wall hole made by the needle and progresses to expand the hole to a larger diameter. The catheter is advanced to the desired position in the vessel, and the guide needle withdrawn, e.g., leaving free access to the female luer in the hub. The normally closed valve is closed and no fluids can flow proximally from the catheter. Optionally, a male luer can be present during catheter insertion to open the valve and allow detection of blood as the needle or catheter enters a vein. A device having a male luer fitting (e.g., fluid line or syringe) is inserted into the female luer fitting to contact the proximal contact surface of the adaptor. The male luer is inserted further until it swedges into the female luer (making a primary seal), and in the process presses distally the adaptor. On moving distally, the adaptor torsion bar struts are bent producing a counter force. The adaptor is pushed into the proximal contact surface of the resilient valve, forcing it open and generating a fluid flow path from the luer internal channel, through the adaptor, past the open valve and into the catheter bore. The technician can withdraw and/or inject fluids through the catheter. On completion of the fluid transfer, the technician removes the male luer. As the male luer is withdrawn, the struts urge the adaptor proximally, e.g., allowing the resilient valve to return to the normally closed position.

Figure 8:
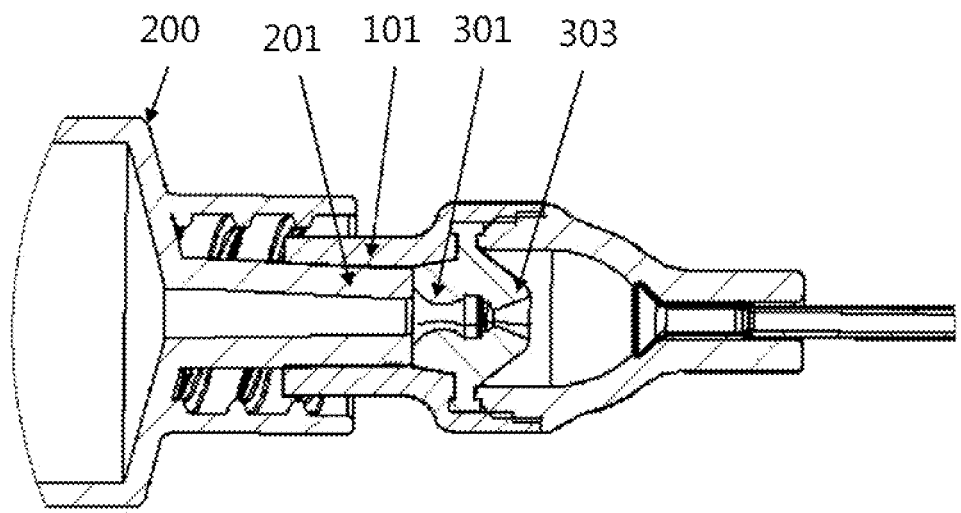
FIG. 8 is a cross sectional diagram showing how distortion of the annular body by pressure from the male luer forces open the valve.
Figure 9:
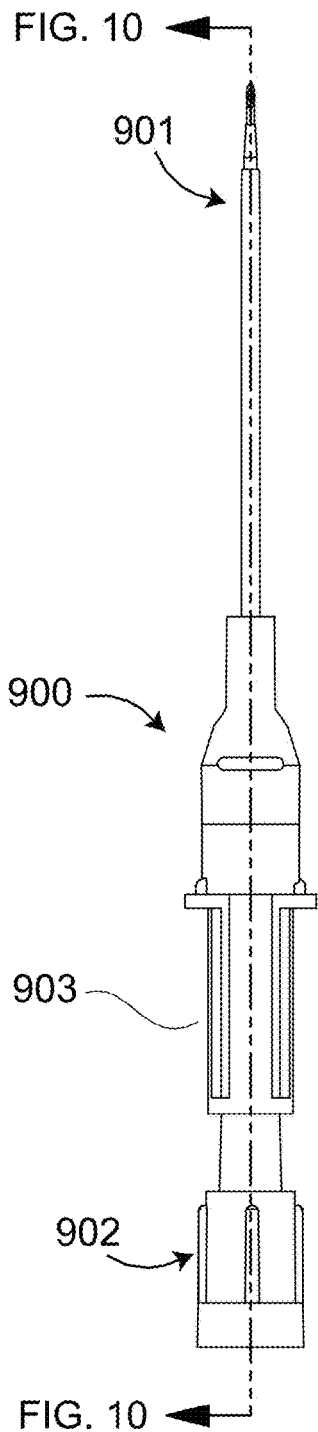
FIG. 9 is a perspective view of an intravenous catheter delivery device 900. The device comprises a first (distal) end 901 for accessing the vascular space via a percutaneous puncture and a second (proximal) end 902 for the containment of the needle like portion of the device. A connecting or middle portion 903 of the device can contain energy storage features, passive activation features; as well as allows for the inclusion of an ergonomic gripping surface or feature.
Figure 10:
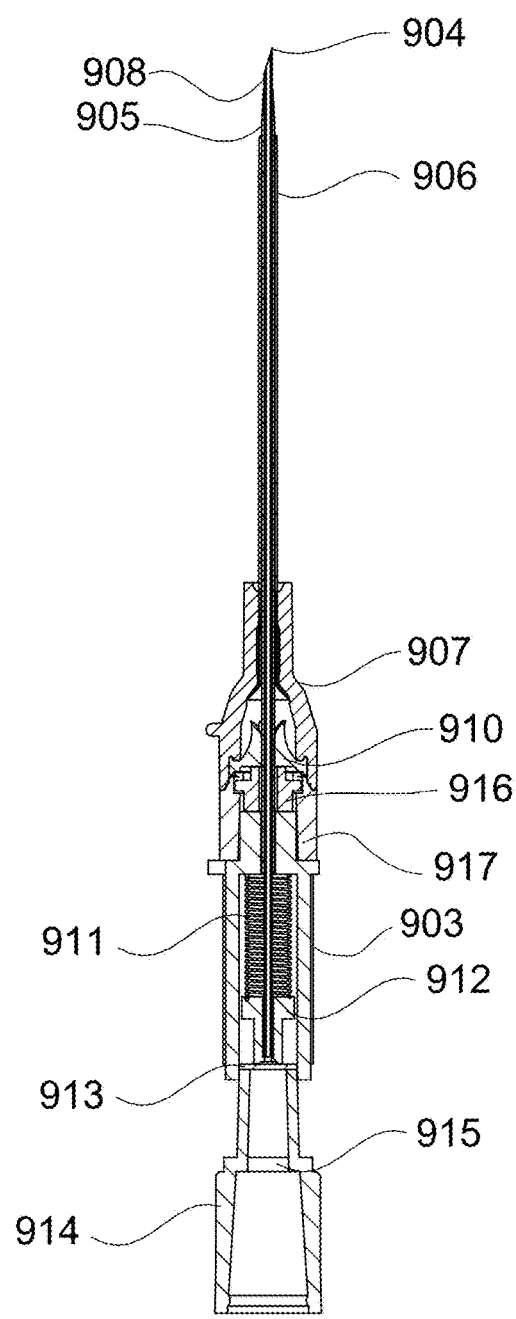
FIG. 10 is a profile view with an axial cross-section view of the FIG. 9 embodiment configured in its "out-of-the-box" condition. The first end 901 comprises a hollow needle 908 with an exposed end that has been ground into a beveled needle tip 904. The needle 908 is surrounded by multiple layers of material concentric to its long axis. These layers may include one or multiple dilators 905 that serve to increase the caliber of a puncture wound in order to facilitate the introduction of a co-radially loaded catheter 906. The catheter 906 is attached to a catheter hub 907 that includes accommodations for an enclosed or otherwise fixed valve 910. A valve actuator 916 is in actuator hub 917. The catheter hub and/or the actuator hub can have threading features to receive standard or custom twist locking devices and accessories as well as having internal configurations to seal around a luer tip. A spring 911 is contained in the middle portion 903. The spring is typically compressed to store energy to carry out a needle retraction function. The spring 911 engages with a needle hub 912 that receives the proximal end of the needle 908. The needle hub 912 is in contact and is maintained in position by a membrane 913. This membrane can provide the function of a blood activated passive safety trigger. The proximal end 902 of the device can include a handle cap 914 or other needle container which can include features such as a foam plug 915 that allows for venting of entrapped gases.
Figure 11:
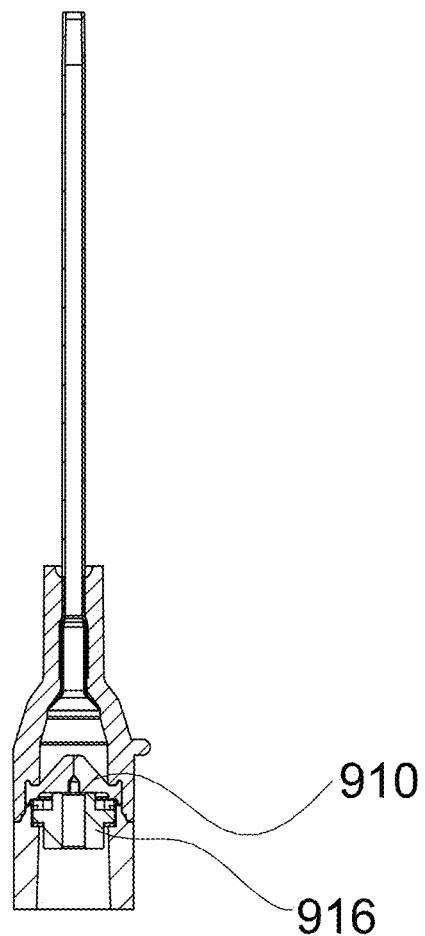
FIG. 11 is a perspective view of intravenous catheter delivery device distal catheter and valve/actuator elements. In this figure the first end has been dismounted from the second end of the device. This figure provides a profile cross-section view of FIG. 9 structures. This shows the valve 910 and the luer-activated valve actuator 916 in there hemostasis (closed) position. This is the position in which the components would be when the intravenous catheter is providing venous access with the needle bearing section of the device removed.
Figure 12:
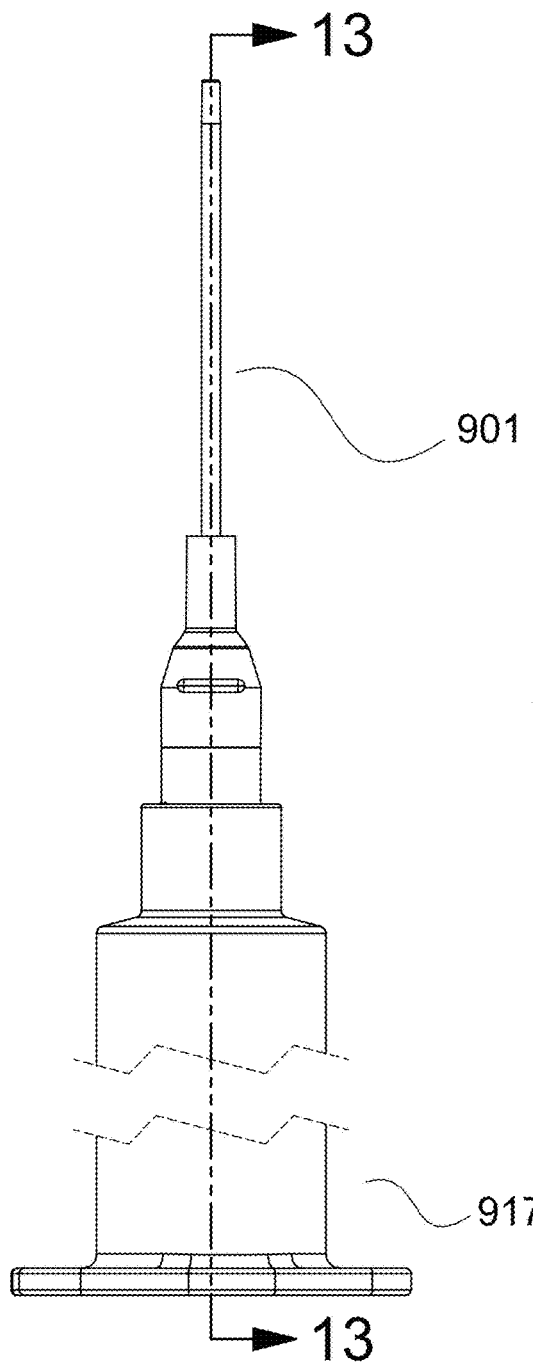
FIG. 12 shows the first end 901 engaged with an ISO 594 compatible luer equipped syringe 917.
Figure 13:
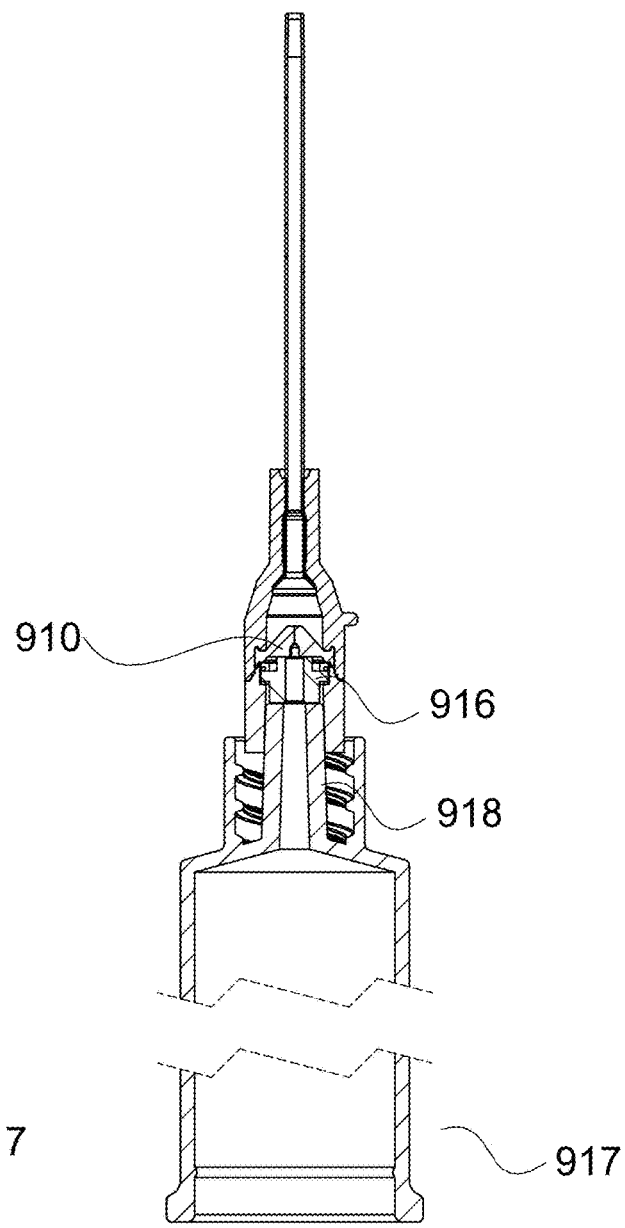
FIG. 13 provides a cross-section view of the FIG. 12 embodiment. In this position, the luer 918 of the ISO 594 compatible luer equipped syringe 917 has come in contact with the valve actuator 916 but was not actuated the valve 910.
Figure 16:
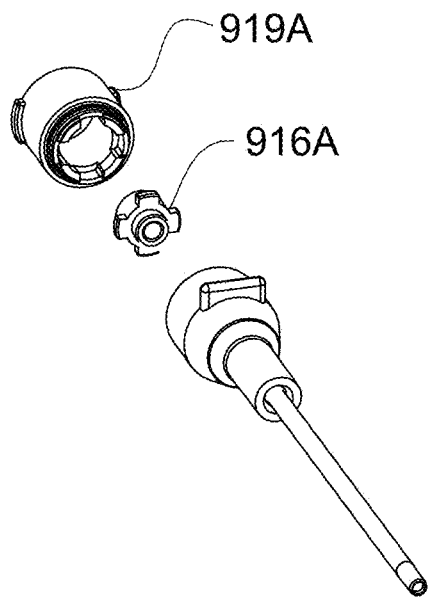
FIG. 16 shows an exploded isometric view of a first end 901. The valve actuator 916 can be seen to have 4 legs that engaged (e.g., legs into slots) with an ISO 594 compatible female luer 919A (actuator hub).
Figure 17:
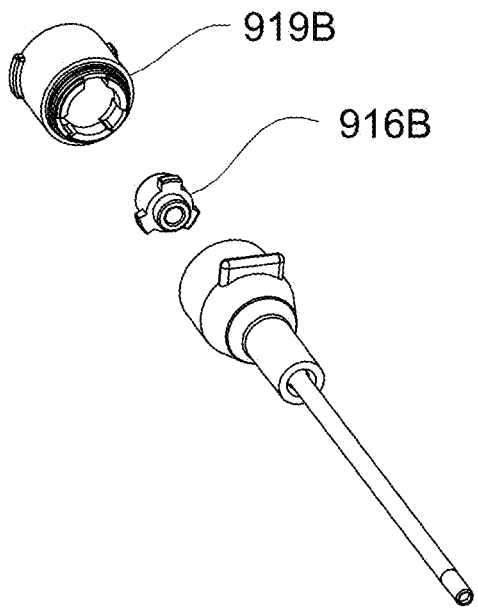
FIG. 17 shows an exploded isometric view of a first end 901. In this embodiment, the valve actuator 916B can be seen to have 3 legs engaged with an ISO 594 compatible female luer 919B.
Figure 18:
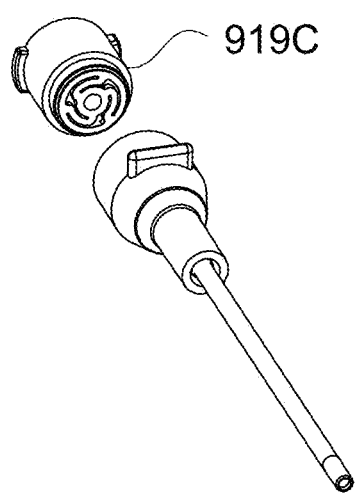
FIG. 18 shows an exploded isometric view of the first end 901. In this embodiment, the valve actuator is shown integrated into an ISO 594 compatible female luer 919C. The strut mounted actuator is unitary with the actuator hub.
Figures 19, 20, 21:
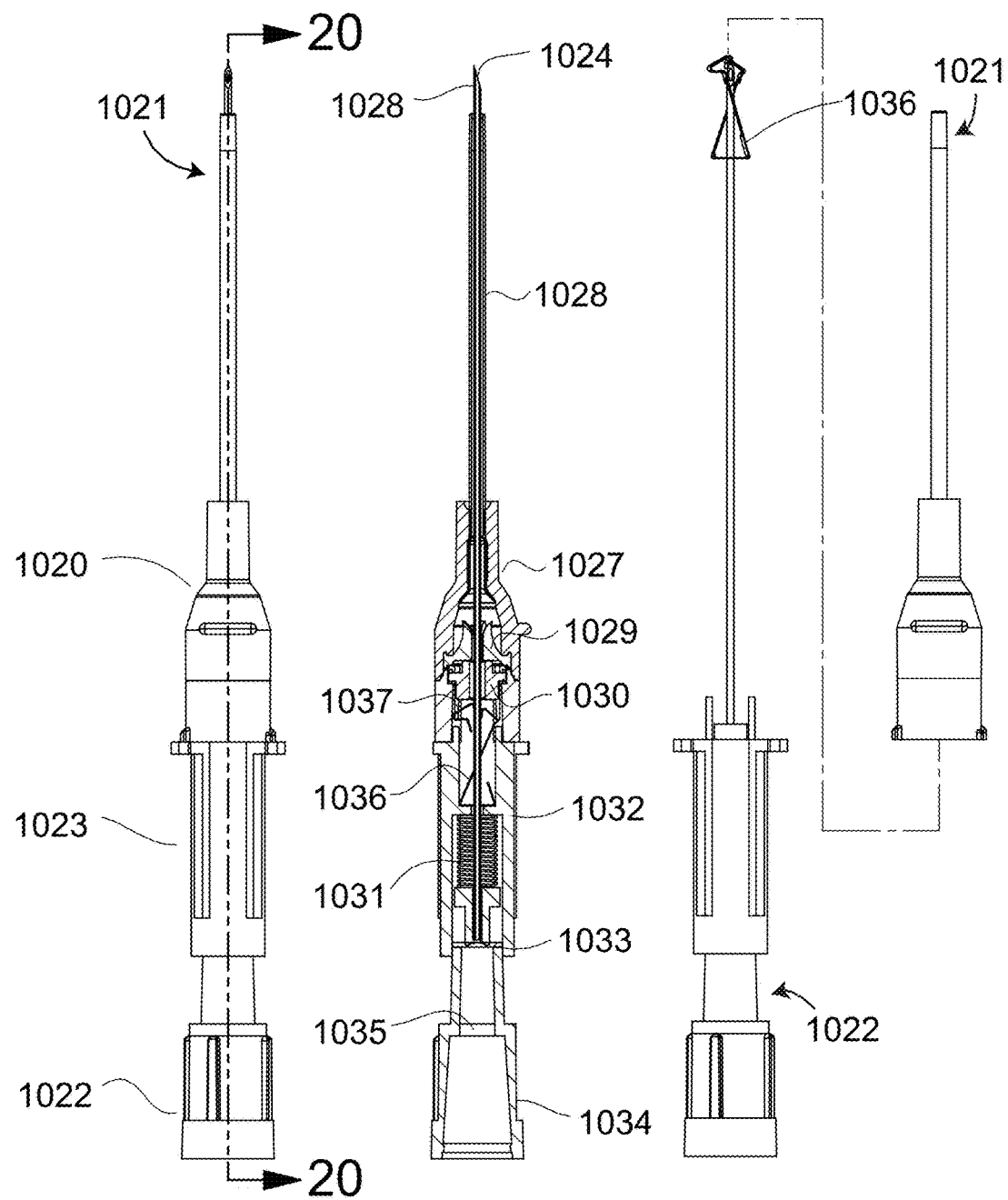
FIG. 19 is a perspective view of another intravenous catheter delivery device 1020. The device comprises a first end 1021 for accessing a vascular space via a percutaneous puncture and a second end 1022 for the containment certain needle-associated structures in the device. A connecting or middle portion 1023 of the device can contain energy storage features, and/or passive activation features, as well as allowing for the inclusion of an ergonomic gripping surface or feature.
FIG. 20 provides a cross-section view of the FIG. 19 embodiment configured in its "out-of-the-box" condition. A first end 1021 comprises a hollow needle 1028 with an exposed end that has been ground into a beveled piercing tip 1024. The needle 1028 is surrounded by a co-radially loaded catheter 1026. The catheter 1026 is attached to a catheter hub 1027 that includes accommodations for an enclosed or otherwise fixed valve 1029, a valve actuator 1030, and exterior threading features to receive standard or custom twist locking devices and accessories, as well as internally configured to seal around a luer tip. A sliding safety clip 1036, is initially contained in the middle portion 1023, but can move axially along the needle and can be activated passively (e.g., captured at the needle tip) as the first end 1021 is dismounted from the second end 1022. This sliding safety clip 1036 disengages from features in the ISO 594 compatible female luer 1037 in order to deploy. A spring 1031 is contained in the middle portion 1023 to store energy available for activation of a function, such as needle retraction. The spring 1031 engages with a needle hub 1032 that can serve as an attachment point to the needle 1028. The needle hub 1032 is in contact and is maintained in position by a membrane 1033. This membrane provides the function of a blood activated passive safety trigger, e.g., to retract the needle on entry of the needle tip into a blood vessel. The proximal end 1022 of the device is defined by a handle cap 1034 or other needle container which can include features such as a gas porous plug 1035, allowing for venting of gases.
FIG. 21 presents another iteration of an intravenous catheter delivery device. In this figure the first end 1021 has been dismounted from the second end 1022 of the device. The sliding safety clip 1036 has moved distally and covers the beveled end 1024 of the needle 1028 providing needle stick safety.

In some embodiments, the resilient valve includes the annular body feature. In such cases, either the adaptor or male luer can provide the contact, pressure, and throw that opens the valve. At a step where the normally closed valve is forced open, the male luer or adaptor presses against the proximal contact surface of the annular body. The annular body distorts so that annular body material is forced distally exerting leverage in the valve material at a pivot point at the base of the valve cusps, forcing open the valve (e.g., as shown in FIG. 8). The technician can withdraw and/or inject fluids through the catheter. On completion of the fluid transfer, the technician removes the male luer. As the male luer is withdrawn, the resilient rebound of the annular body removes the opening force, allowing the valve to return to the normally closed position.

EXAMPLES

The following examples are offered to illustrate, but not to limit the claimed invention.

Example 1

Features of High Performance Catheters

Dilator—The use of a dilator allows for the use of smaller caliber needles, which can lead to lower puncture forces required as well as less patient discomfort.

Passive safety feature—This removes the burden from the user to remember to activate a safety feature. The use of the membrane and its location in the fluid path allows the safety feature to respond to the successful access of a vessel by releasing the needle to be retracted. Optionally, the device can have a system to capture a cap over the needle tip as it is removed from the catheter.

Venting—Vents allow the flow of blood through the device and into the membrane, e.g., without blood exiting proximally.

Valve actuator—The devices can be equipped with a valve actuator that transfers the axial motion of the luer tip of a syringe in order to open the valve to flow. This allows the use of syringes with various luer tip lengths to actuate the valve.

Example 2

Methods of Use

One desirable function in the present catheter devices is to provide a passive inadvertent needle stick safety feature to an intravenous catheter while creating a secure and hemostatic peripheral venous, central venous or arterial access site.

After disinfection of the puncture site and removal of a protective cap from the needle, a suitable vein can be punctured. If venipuncture was successful, blood will then travel the length of the needle and present into the flash chamber. The flash chamber fills and then allows some blood to contact the membrane. When the blood soaks into the membrane, it causes it to loss structural strength. The weakened membrane then ruptures and allows the spring to retract the needle into the device rendering it safe to the user.

The catheter can be advanced further into the vein, while still being supported by the dilator. Upon completion of the catheter insertion, the dilator can be pulled out as it is attached to the handle that contains the needle. The device is discarded and the procedure is complete.

In some cases, the needle tip is only retracted within the catheter a short distance. There may or may not be a dilator structure between the needle and catheter. The catheter can be advanced further into the vein, while still being supported by the needle. Upon completion of the catheter insertion, the needle can be pulled fully out as it is attached to the handle (e.g., needle hub). As the needle is extracted, the safety clip stays in a fixed position in the hub. When the needle bevel tip passes thru the distal end of the safety clip, the clip closes, rendering the device safe to the user. The device can be discarded and the procedure is complete.

Example 3

Adaptors to Receive Various Male Luer Fittings

In one embodiment of the invention an adapter is integrated into the proximal end of the catheter hub as shown in FIGS. 1-4.

FIG. 1 shows a cross section of the IV catheter 100 assembled with the catheter hub female luer 101, the pressure activated valve 110, the distal catheter hub 120, and the flexible IV catheter 130. Together, the catheter hub female luer and distal catheter hub make up the catheter hub assembly 140, and are bonded together with adhesive or by ultrasonic or spin welding, or may have a snap fit.

Figure 2:
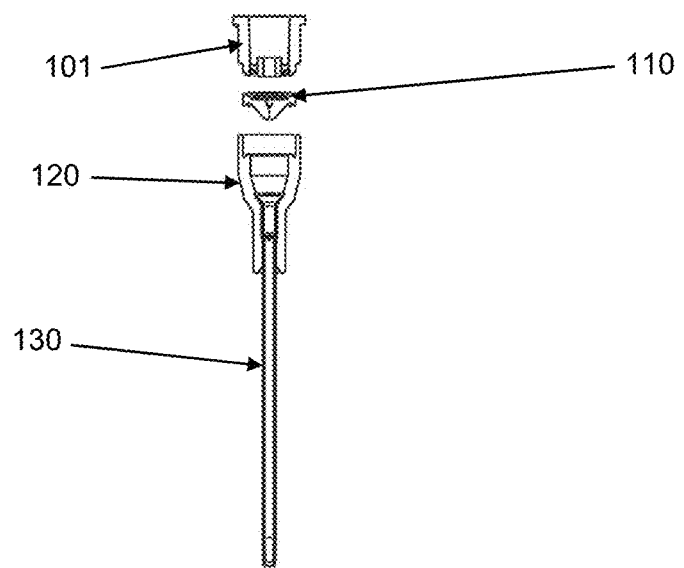
FIG. 2 is a cross-sectional showing an exploded version of the catheter assembly, including a unitary hub adaptor.

FIG. 2 shows an exploded view of the assembly in FIG. 1.

Figure 3:
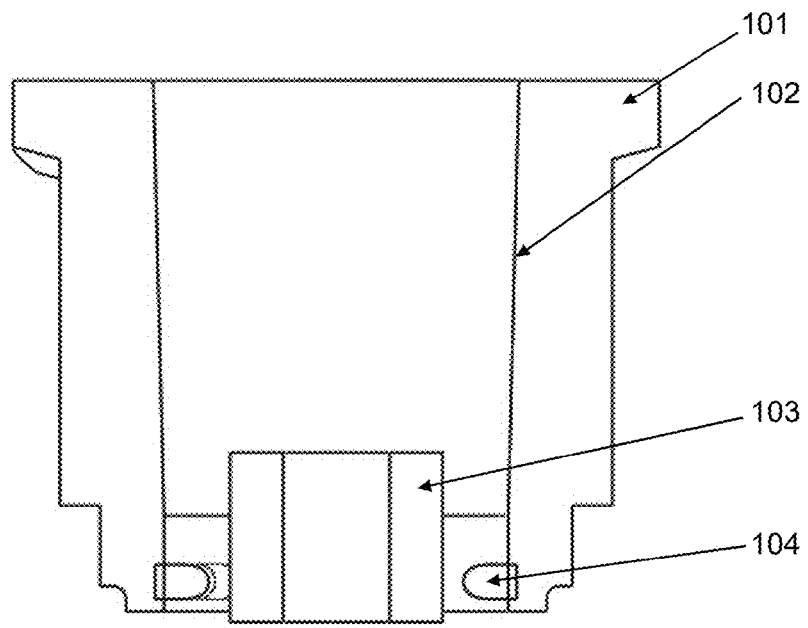
FIG. 3 is a diagram showing a cross-section of a unitary hub/strut/adaptor device.

FIG. 3 is a detail view of the catheter hub female luer 101, showing the tapered bore 102 that is dimensionally sized to the ISO standard for a female luer. Near the distal end of the female luer, the adapter 103 is held in position within and concentric with the bore of 101 by the struts 104.

Figure 4:
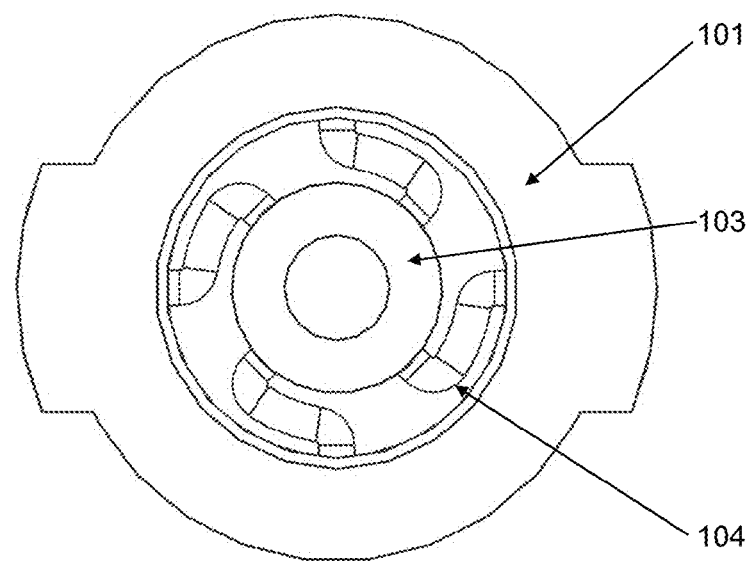
FIG. 4 is a diagram of an end-on view of an adaptor suspended in a hub by struts.

FIG. 4 is an axial view of the catheter hub female luer 101 looking in the distal direction, showing the struts 104 as having a circular cross section and serpentine path in connecting the adapter to the hub. Other embodiments may incorporate struts with different cross sectional shapes and paths to connect the adapter to the hub. The struts serve to not only integrate the catheter hub female luer and adapter section into a single component, but to provide for axial movement of the adapter as an IV fitting, luer connector, or syringe is inserted into the proximal end of the catheter.

Figure 6:
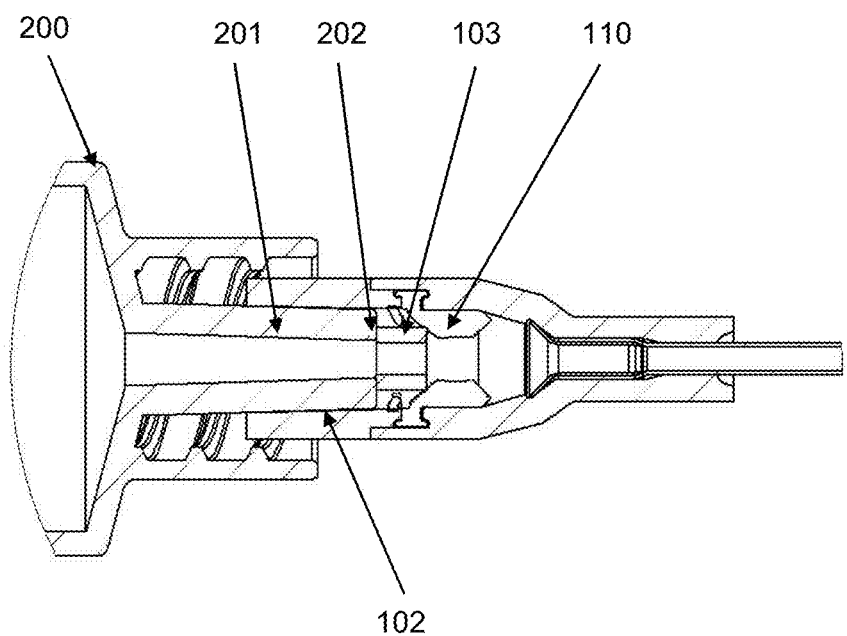
FIG. 6 is a cross sectional diagram showing a male luer device (syringe) pressing the adaptor to force open the valve.

FIG. 5 is a partial sectional view of IV catheter 100 with the distal end of a syringe 200 inserted into the catheter hub female luer. Once fully inserted, as shown in FIG. 6, the male luer 201, with its tapered outside diameter, seals against the tapered inner bore 102 of the catheter hub female luer, at which point the distal tip 202 of the male luer axially displaces the adapter 103 distally against the first recess in the proximal face of the valve, which forces the valve to open.

The adapter is generally cylindrical in shape and the distal end of the adapter (i.e. the end that contacts the proximal side of the valve) may have radiused edges. The outside diameter of the adapter, and particularly the proximal end of the adapter, is smaller than the outside diameter of the male luer, but larger than the inside diameter of the distal tip of the male luer of e.g. the IV fittings, luer connectors, or syringes used to administer therapy through the catheter into the patient's vasculature. The axial displacement of the adapter causes the struts to deflect and are thereby subjected to torsional forces through their cross sections.

Upon withdrawal of the male luer from the proximal end of the catheter, the torsional forces that acted on the struts during the axial displacement of the adapter are released and force the adapter to move axially away from the valve, permitting its closure.

The length and position of the adapter within the proximal end of the catheter hub is established so as to accommodate various male luer geometries and provide the mechanical pressure to force the valve to open and close. Male luers with relatively short insertion depths into the catheter hub will cause sufficient displacement of the adapter to open the valve. Male luers with longer insertion depths will not only open the valves, but due to the relatively small outside diameter of the adapter as compared with the moving parts of the valve, the longer axial displacement of the adapter into the valve does not cause damage to, or interfere with the functioning of the valve.

Example 4

Resilient Adaptors

Male luer geometry variations can be optionally accommodated by use of an annular body in the resilient valve, as shown in FIG. 7. Here, the proximal end of the valve 300 is modified relative to the embodiment described above or the valve in US patent application US-2013-0204226-A1, in that the recess(es) in the proximal surface of the valve are replaced by valve material 301 that extends proximally from that surface to some distance into the proximal end of the catheter hub. A tapered recess or counterbore 302 in the center of added valve material provides a fluid flow path through the proximal end of the valve.

As noted above, FIGS. 6 and 7 illustrate that the devices can be used in methods of injecting or withdrawing fluids with a male luer device 201, an annular body 301 on the proximal side of the valve 350 interacts with the male luer 201 to force open the normally closed valve. For example, the self-closing valve can include a proximal annular body 301 defining a proximal tapered recess 302, distal convex surface 352, and one or more slits 354 in the distal surface running to the proximal tapered recess and defining two or more cusps 303. Optionally, the valve 350 can include a radial mounting flange 356. In many embodiments, the valve is a unitary structure made of a resilient material. The annular body can have a proximal contact surface comprising an outer diameter and an inner diameter, wherein the inner diameter is less than an outer diameter of a standard male luer fitting distal surface, e.g., so that the contact surface matches up to receive forces from the luer fitting. The valve can be adapted so that when the proximal contact surface is forced distally the resilient material of the valve distorts to separate the two or more cusps, creating a path of fluid flow between the proximal recess and the distal surface. The valve is typically mounted between a female luer hub and the catheter section. The valve is usually a resilient normally closed cusp valve.

In FIG. 8, when, e.g. an IV fitting, luer connector, or syringe 200 luer is inserted into the female luer 101 of the catheter hub, the male luer 201 presses against the material that now extends proximally from the valve 301. The elastomeric material of which the valve is composed responds to the contact with the male luer in two ways: The material deforms, causing it to partially fill the tapered recess or counterbore described above as shown in FIG. 8; but it also transmits the mechanical pressure from the male luer to the lobes of the valve 303, causing them to pivot radially and thereby opening the valve. Within the range of male luer geometry manufactured by the industry the valve material responds more or less as the material illustrated in FIG. 8.

As the male luer is withdrawn from the catheter hub, the valve material responds elastically to return to its original sealed condition. The tapered outside diameter of the proximal valve extension follows the shape of the inside diameter of the proximal end of the catheter hub, providing additional forces to urge the valve lobes to close concentrically and completely.

Example 5

Other Features

The catheter hub adapter as discussed above and shown in FIGS. 1-4 may have a tapered or funnel shape such that the proximal end (the end contacted by the male luer) has a larger inner and/or outer diameter than the distal end (the end that contacts the valve). Such a design may require less force to open the valve and may further reduce the risk of damaging the valve when long male luers are inserted into the catheter hub and displace the adapter more than is nominally expected.

The cross-sectional shape of the struts may be round, oval, rectangular or a combination of shapes to enhance the strength and moldability of the part. Similarly the path that the struts follow in connecting the adapter to the proximal section of the catheter hub may be any of a variety of curvo-linear patterns to enhance strength and moldability. As few as two may be used to secure the adapter to the catheter hub female luer, and a plurality of struts may be used, limited in number by complexity and manufacturability.

It is envisioned that an adaptor can be used to contact the proximal contact surface of an annular body to open valves with this feature.

Example 6

Modifications, Manufacture, and Alternatives

Gripping Surface—In the figure descriptions, a gripping means may be any of a number of surface effects including, but not limited to, embossed, or debossed features, surface finish and over-molded or two-shot features. Textures, resiliency, and contours can be employed to provide more confident manipulation of the present devices.

Energy storage feature—In the figure descriptions, a means of storing energy is typically shown as a helical spring. Other methods may be used to store energy such as, e.g., compressible or stretchable polymers, expandable polymers, pressurized gas or liquid or molded plastic features. Optionally, actuation can be by expansion of foams or polymers on hydration or exposure to heat.

Valve Actuator—In the figure descriptions, an activation means for the valve typically engages the internal structure of the luer via four contact points. However, any number and shape of contact points that would allow the relative movement of the actuator and the luer are possible. The valve actuator may also be integrally molded into the female luer portion of the catheter hub. This integral actuator may be connected to the inside surface of the luer at a single or multiple points.

Bonding—Adhesives may be employed to substantially join components. Adhesives may be but are not limited to: cyanoacrylate, 2-part epoxy, heat-activated resin, UV cured adhesive and hot melt. Joining may also be achieved through, but not limited to, the use of solvent bonding, frictional welding, ultrasonics, and heat-staking means.

Injection molding—Any of the proposed device components can optionally can be injection molded. Design intent may be such that designs are molded with simple open/close tooling to reduce tool cost and cycle times.

Coil winding—Spring components may be manufactured by coil winding spring tempered wire.

Component coupling—Where feature definition of a component is not readily achieved by single tool molding; ultrasonic welding, adhesives, or mechanical retention may be employed to join components. Furthermore, where combinations of different materials may be advantageous, a two-shot molding technique may be utilized.

Example 7

Modular Actuator

The valve actuator can function to transfer the force of, e.g., luer insertion to a catheter hub, to the proximal end of a resilient valve. The distal end of the actuator can be optimally configured to interact with the valve, and the proximal end of the actuator can be configured to effectively receive a broad array of different male fittings. Optionally, the actuator can be an integral or fitted part of in its own hub. The actuator hub can include external twist fittings and/or internal contours adapted to standard connectors, such as male luer parts.

There can be advantages to moving the actuator back into a separate hub, so that it could be manufactured with molded parts for high volume manufacturing. Such an arrangement can allow for separate manufacture of finely detailed actuators, from specialized materials, and ready insertion into an overall catheter hub/actuator hub framework. For example, separately manufactured valves and actuators can be pressed into their respective hubs then functionally associated by fitting the hubs together.

In FIG. 22A, catheter hub 1027 has received resilient valve 1010 into an annular snap-fit socket. Two legged actuator 1016 can be nested into position in actuator hub 137, which also includes a female luer feature.

FIG. 22B shows how the components are associated on completed assembly. The device is shown in the relaxed position, without the needle present. Note that introduction of a male luer into the actuator hub can urge the actuator distally, e.g., with actuator legs (tabs) 1040 sliding within the confines of actuator slots 1041.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of providing fluid contact between a male luer connector and a catheter, the method comprising:
   providing the catheter having a luer connector, and a catheter section;
   wherein the luer connector comprises a female hub having an inner central channel comprising a proximal tapered receiver adapted to receive the male luer connector;
   where the luer connector includes a valve biased against proximal flow such that the valve has a normally closed configuration, the valve comprising: a proximal annular body defining a proximal tapered recess, a medial mounting flange, a distal convex surface, and one or more slits in the distal convex surface running to the proximal tapered recess and defining two or more cusps;
   inserting the male luer connector into the proximal tapered receiver until a distal end of the male luer connector contacts a proximal contact surface of the proximal annular body of the valve; and,
   further inserting the male luer connector, distorting the proximal annular body causing a portion of the proximal annular body to partially fill the proximal tapered recess, which transmits a force distally to radially displace the two or more cusps thereby opening the valve and creating a path of fluid contact between the male luer and the catheter.

2. The device of claim 1, wherein the valve is fabricated from a resilient material.

3. A self-closing valve device comprising:
   a proximal annular body defining a proximal tapered recess;
   a radially disposed mounting flange;
   a distal convex surface;

one or more slits in the distal convex surface running to the proximal tapered recess and defining two or more cusps; and wherein the proximal annular body is configured such that where a compressive force applied to the proximal annular body causes the proximal annular body to distort and partially fill the proximal tapered recess, which causes radial displacement of the two or more cusps to create a fluid path through the self-closing valve.

4. The device of claim 3, wherein the proximal annular body comprises a unitary structure made of a resilient material.

5. The device of claim 3, wherein the proximal tapered recess further comprises a proximal contact surface comprising an outer diameter and an inner diameter defining the proximal tapered recess; wherein the inner diameter is less than an outer diameter of a male luer fitting.

6. The device of claim 3, wherein the distal convex surface comprises a conical surface.

7. The device of claim 3, further comprising a catheter section positioned distal from the valve and comprising a catheter hub and catheter.

8. The device of claim 3, wherein the self-closing valve device is mounted between a female luer hub and the catheter section.

* * * * *

UNITED STATES PATENT AND TRADEMARK OFFICE
CERTIFICATE OF CORRECTION

PATENT NO. : 10,052,474 B2
APPLICATION NO. : 14/660151
DATED : August 21, 2018
INVENTOR(S) : Stephen R. Keyser et al.

Page 1 of 1

It is certified that error appears in the above-identified patent and that said Letters Patent is hereby corrected as shown below:

In the Specification
In Column 14, Line 50, please replace "1 mm If" with --1 mm. If--;
In Column 14, Line 60, please replace "1 mm The" with --1 mm. The--;
In Column 14, Line 62, please replace "3 mm" with --3 mm.--; and
In Column 16, Line 5, please replace "1 mm" with --1 mm.--.

Signed and Sealed this
Seventh Day of May, 2019

Andrei Iancu
*Director of the United States Patent and Trademark Office*